(12) United States Patent
Björling et al.

(10) Patent No.: US 8,131,366 B2
(45) Date of Patent: Mar. 6, 2012

(54) BIVENTRICULAR HEART STIMULATOR AND METHOD OF CONTROLLING A BIVENTRICULAR HEART STIMULATOR

(75) Inventors: Anders Björling, Järfälla (SE); Nils Holmström, Järfälla (SE)

(73) Assignee: St. Jude Medical AB, Jarfalla (SE)

( * ) Notice: Subject to any disclaimer, the term of this patent is extended or adjusted under 35 U.S.C. 154(b) by 835 days.

(21) Appl. No.: 11/885,326

(22) PCT Filed: Mar. 2, 2005

(86) PCT No.: PCT/SE2005/000313
§ 371 (c)(1),
(2), (4) Date: Sep. 22, 2008

(87) PCT Pub. No.: WO2006/093442
PCT Pub. Date: Sep. 8, 2006

(65) Prior Publication Data
US 2009/0076560 A1      Mar. 19, 2009

(51) Int. Cl.
*A61N 1/37* (2006.01)
(52) U.S. Cl. .......................................................... 607/28
(58) Field of Classification Search .................. 607/4, 5, 607/25, 28
See application file for complete search history.

(56) References Cited

U.S. PATENT DOCUMENTS

| 6,618,622 | B1 | 9/2003 | Mann et al. |
| 2001/0049542 | A1 | 12/2001 | Florio et al. |
| 2003/0195579 | A1 | 10/2003 | Bradley et al. |
| 2003/0204214 | A1 | 10/2003 | Ferek-Patric |
| 2004/0260352 | A1 | 12/2004 | Rueter et al. |
| 2008/0071319 | A1 * | 3/2008 | Sathaye et al. ................... 607/28 |

FOREIGN PATENT DOCUMENTS

| EP | 1 430 931 | 6/2004 |
| EP | 1 155 711 | 11/2005 |
| EP | 0 990 451 | 3/2006 |
| WO | WO 2004/026398 | 4/2004 |

* cited by examiner

Primary Examiner — Brian T Gedeon
(74) Attorney, Agent, or Firm — Schiff Hardin LLP

(57) ABSTRACT

In a biventricular heart stimulator and a method for controlling such a biventricular heart stimulator, successive stimulation pulses are delivered to the ventricles of a heart such that stimulation pulses in a single heartbeat cycle are respectively first delivered to the first ventricle and then to the second ventricle. Capture or loss of capture in response to stimulation pulses delivered to one ventricle is detected. As a result of a detected loss of capture, preventative measures are taken for preventing loss of capture in the other ventricle.

28 Claims, 5 Drawing Sheets

BIVENTRICULAR HEART STIMULATOR AND METHOD OF CONTROLLING A BIVENTRICULAR HEART STIMULATOR

BACKGROUND OF THE INVENTION

1. Field of the Invention

The present invention generally relates to the field of implantable heart stimulation devices, such as pacemakers. More specifically, the present invention relates to a biventricular heart stimulator for stimulating both ventricles of a human heart and a method for controlling such a stimulator.

2. Description of the Prior Art

In a normal human heart, the sinus node, generally located near the junction of the superior vena cava and the right atrium, constitutes the primary natural pacemaker initiating rhythmic electrical excitation of the heart chambers. The cardiac impulses arising from the sinus node are transmitted to the two atrial chambers, causing depolarizations known as P-waves, which result in atrial chamber contractions. The excitation pulses are further transmitted to and through the ventricles via the atrioventricular (A-V) node and a ventricular conduction system, causing depolarizations known as R-waves which result in ventricular chamber contractions. An R-wave is also referred to as a QRS complex.

Implantable pacemakers generate electrical stimulation pulses and deliver such stimulation pulses to atrial and/or ventricular muscle tissue of a patient's heart at a prescribed rate and/or rhythm when, through disease or other causes, the heart is not able to maintain the prescribed heart rate or rhythm on its own. When the delivered electrical stimulation pulses are of sufficient energy, they cause the cardiac muscle tissue to depolarize, and therefore contract, thereby forcing the heart rate or rhythm to track the delivery of the stimulation pulses. When the delivered stimulation pulses are of insufficient energy, depolarization does not occur, and the heart rate or rhythm is not controlled by the pacemaker. Hence, for the pacemaker to perform its intended function, it is critically important that the delivered electrical stimulation pulses be of sufficient energy to depolarize the cardiac tissue.

The depolarization and ensuing contraction of the heart in response to a delivered cardiac stimulation pulse is generally referred to in the art as "capture". Consequently, the term "non-capture" denotes the condition when a delivered stimulation pulse does not result in depolarization and contraction. When detecting capture, sensing circuitry checks for the depolarization of a cardiac chamber following and in response to a delivered stimulation pulse. Such a depolarization as a result of a delivered stimulation pulse is also referred to as an "evoked response" (ER) of that chamber. Furthermore, evoked response is detected during a selected time period following the delivery of a stimulation pulse. Such a time period is generally referred to as an "evoked response window".

The energy of the electrical stimulation pulses generated by an implanted pacemaker is derived from the energy stored in the pacemaker power source or battery. The pacemaker battery has a limited amount of energy stored therein, and the generation of stimulation pulses represents by far the greatest drain of such energy.

The amount of energy needed to effectuate capture is known as the capture "threshold". Hence, stimulation pulses of energy less than the capture threshold do not bring about capture, while stimulation pulses of energy greater than the capture threshold do bring about capture. By adjusting the energy of the electrical stimuli so that it is always greater than the capture threshold, but not too much greater, the limited energy of the pacemaker battery may thus be preserved. The battery energy is preserved for two reasons. Firstly, pulses having an energy content insufficient to cause capture, i.e. stimulation pulses below threshold level, are rarely generated. Such pulses represent wasted energy. Secondly, pulses having an excessive energy content, i.e. an energy content greatly exceeding the capture threshold, are also rarely generated. Such excess energy does not only represent wasted energy, but also energy that may disadvantageously cause pectoral stimulation and/or sensation.

Generally, a capture threshold search is performed at predetermined or preprogrammed intervals. A capture threshold search would begin at a desired starting point (either a high energy level or the level at which capture is currently occurring) and decrease the energy level until capture is lost. The value at which capture is lost is known as the capture threshold. Thereafter, in order to secure capture, a safety margin is added to the capture threshold to arrive at the energy content of the stimulation pulse. One of the key issues is to choose the safety margin such that it provides capture, while at the same time provides adequate energy savings and does not cause pectoral stimulation and/or sensation.

A single-chamber pacemaker delivers pacing pulses to one chamber of the heart, either one atrium or one ventricle, via either a unipolar or bipolar lead. Single-chamber pacemakers can operate in either a triggered mode or a demand mode. When operating in a demand mode, sensing and detection circuitry allow for the pacemaker to detect if an intrinsic cardiac depolarization, either an R-wave or a P-wave, has occurred within the defined timeout interval. If an intrinsic depolarization is not detected, a pacing pulse is delivered at the end of the time-out interval. However, if an intrinsic depolarization is detected, the pacing pulse output is inhibited to allow the natural heart rhythm to preside.

Biventricular pacemakers are now available and can provide either demand or trigger type pacing in both the right and the left ventricular chambers. In biventricular pacing, one bipolar lead is typically placed in the coronary sinus for pacing and sensing in the left ventricle. Another bipolar lead is positioned in the right ventricle for pacing and sensing in the right ventricle.

Generally, capture verification occurs on a beat-by-beat basis. If no capture is verified, i.e. a loss of capture is detected, the pacemaker provides a backup pulse with an increased energy content. If successive losses of capture are detected, this indicates that an increase in capture threshold has occurred. Then, the pacemaker responds by performing a threshold search, and sets the energy level of the successive stimulation pulses to the new capture threshold plus the added safety margin.

In a cardiac stimulation device arranged for biventricular stimulation, the stimulation threshold and the evoked response are measured both in the first and the second stimulated ventricle. However, a problem with known biventricular pacemakers equipped with features to assure capture after stimulation pulses, is that it is difficult to verify capture on every beat, particularly if the pacemaker operates with a delay between the first stimulation pulse delivered to the first ventricle and the last stimulation pulse delivered to the second ventricle. Such a delay is known as an interventricular delay or interval, or a VV delay, and is generally provided in order to control the contractions of the ventricles in desired manner.

After a delivered stimulation pulse, the evoked response detection window typically ends 50-100 ms after the stimulation. Thus, an interventricular delay chosen such that the stimulation pulse is delivered to the second ventricle during this period, will result in an interference with the detection of the evoked response resulting from a delivered stimulation pulse in the first ventricle. In other words, it would be difficult to verify loss of capture.

One attempt to address this problem has been to only verify capture or loss of capture in the second ventricle on a beat-by-beat basis. Thus, capture is not usually verified on a beat-by-beat basis in the first ventricle, but rather after certain programmable time intervals, for instance every 15 minutes or 1 000 heartbeats. At these instants, the evoked response (ER) window for the first ventricle is normally made clear from disturbing stimulation pulses in other places of the heart by a temporarily changed timing pattern for the delivery of stimulation pulses. For instance, the order of delivering stimulation pulses to the first and second ventricle could be shifted, the stimulation pulses could be simultaneous, or the time interval between the pulses to first and second ventricle, known as the interventricular delay, could be adjusted. When losses of capture is detected in the first ventricle, a capture threshold search is performed in order to adjust the stimulation level, if necessary, to the changed capture threshold.

To ensure capture between these capture verifications for the first ventricle, a fixed safety margin is introduced. This safety margin for the first ventricle is normally higher than the safety margin in the second ventricle to account for the fact that the capture verification is not performed on a beat-by-beat basis in the first ventricle.

Changes in capture threshold is normally very slow and the increased safety margin for the first ventricle is normally sufficient to avoid loss of capture in spite of the time period provided between successive capture verifications for the first ventricle. However, studies have shown that during rapid changes in the capture threshold, time periods without capture occur for the first ventricle. If this happens, there is a chance that the patient will not receive the intended cardiac therapy, which in turn can impair the ability of the patient to perform work and deteriorate the state of the heart disease. Such rapid changes could for instance be due to infections, metabolic changes, or medical drugs.

SUMMARY OF THE INVENTION

An object of the present invention is to address the above-mentioned problem of time periods with capture losses in a biventricular heart stimulator.

According to one aspect of the present invention, the above object is achieved by a biventricular heart stimulator for stimulating both ventricles of a human heart having a pulse generator for delivering stimulation pulses of varying amplitudes, and electrode leads for transmitting stimulation pulses from the pulse generator to a first and to a second of said ventricles, and for transmitting electric signals from the ventricles of the heart to the heart stimulator. The stimulator also has a control unit for controlling the pulse generating means, the control unit being configured to control the delivery of the pulses such that stimulation pulses in a single heart beat cycle are respectively first delivered to the first ventricle and then to the second ventricle. Furthermore, the stimulator has a sensing circuit arranged to check for capture or loss of capture in one of the ventricles in response to delivered stimulation pulses, the sensing circuit being controlled by the control unit and arranged to receive the electric signals transmitted by said electrode leads. Moreover, the control unit is arranged to perform as a result of loss of capture determined in one ventricle by the sensing circuit, preventive measures for prevention of loss of capture in the other ventricle, preferably as a result of at least two successive losses of capture.

According to another aspect of the present invention, there is provided a method of controlling a biventricular heart stimulator for stimulating both ventricles of a human heart. The method includes the steps of delivering successive stimulation pulses to a first ventricle and a second ventricle of the heart such that stimulation pulses in a single heart beat cycle are respectively first delivered to the first ventricle and then to the second ventricle, and determining capture or loss of capture by the heart in response to stimulation pulses delivered to one of said ventricles. Moreover, the method includes performing, as a result of detected loss of capture in one ventricle, preventive measures for prevention of loss of capture in the other ventricle. The preventive measures are preferably performed as a result of at least two successive losses of capture in the one ventricle.

Thus, the present invention is based on the insight that changes in capture threshold for one ventricle often are correlated to changes in capture threshold for the other ventricle. When losses of capture occurs in one of the ventricles, this may be an indication that losses of capture are also occurring in the other ventricle. Such losses of capture can be temporary losses of capture, or due to changes in the capture threshold. Regardless of which, losses of capture in one ventricle, triggers actions to be taken for preventing repetitious losses of capture in the other ventricle. Thereby, repetitious losses of capture in the ventricle for which capture or loss of capture can not be determined on beat-by-beat basis, may be significantly reduced or eliminated. As a result, the intended cardiac respiratory therapy (CRT) may be provided, and deterioration of the heart disease due to capture losses is reduced or avoided.

As has been described above, for certain interventricular delays, the delivery of stimulation pulses in the second ventricle may prevent or disturb reliable detection of capture in the first ventricle, whereby continuous detection of capture in the first ventricle may be omitted. Therefore, detection of capture is only performed for the second ventricle on a beat-by-neat basis. Thus, according to the present invention, upon detection of capture loss in the second ventricle, actions for preventing losses of capture in the first ventricle are taken. However, it must be noted that the reverse situation might occur, i.e. that in the normal mode of operation, continuous capture detection in the second ventricle is disabled, while continuous capture detection in the first ventricle is enabled.

Thus, in further accordance with the present invention, upon detection of capture loss in the first ventricle, actions for preventing losses of capture in the second ventricle may be taken. For example, if the stimulation pulse delivered to the first ventricle is sufficient to effectuate capture, then the first ventricle would depolarize and an R wave would propagate through the heart tissue. After a certain time delay, the R wave would also have been conducted to the second ventricle. If the stimulation pulse then delivered to the second ventricle would have been unsuccessful in effectuating capture, and the R wave from the first ventricle would have reached the electrode for detecting capture in the second ventricle during the evoked response window thereof, then the conducted R wave could be interpreted as an evoked response in the second ventricle.

In other words, if the interventricular delay is set, for example for reasons of optimizing the cardiac therapy for a particular patient, such that the conducted R wave could be mistakenly be detected as an evoked response during the evoked response window, then the evoked response detection in the second ventricle could be disabled. If capture can be detected in the first ventricle on a beat-by-beat basis, then the present invention is applicable for taking actions for preventing losses of repetitious losses of capture in the second ventricle triggered by detected losses of capture in the first ventricle.

Thus, when loss of capture has been determined for the first ventricle, actions can be taken for the second ventricle in the manner as stated above, e.g. performing an immediate check for capture, increasing the safety margin, decreasing the time between threshold searches, etc. Therefore, the present invention is not limited to performing preventing measures in the first ventricle as a result of detected loss of capture in the second ventricle, but is also applicable and includes performing preventing measures in the second ventricle as a result of detected loss of capture in the first ventricle.

Furthermore, there are a number of different actions or preventive measures that could be taken in order to achieve said improvements, some of which will be presented in the following description. However, it should be noted that the present invention is not restricted to a particular type of preventive measure.

According to one exemplifying embodiment, the action or preventive measure is an immediate or quick check for capture. Thus, when one or more losses of capture has been detected in one of the ventricles, an immediate check for capture is performed in the other ventricle. Of course, measures are taken for enabling said immediate check for capture, such as changing the interventricular delay or omitting the delivery of the stimulation pulse that adversely affects the accuracy of the capture verification. If the immediate check for capture is positive, i.e. capture being verified, then the mode of operation of the stimulator is restored. In other words, the capture on beat-by-beat basis is only preformed for one ventricle.

However, if the immediate check for capture is negative, a back-up pulse may be provided and a threshold search is performed for adjusting the energy content of the ensuing stimulation pulses, if the threshold search indicates that an adjustment is needed. According to one example, the mode of operation for the stimulator is then restored. According to another example, one or more further threshold searches are performed at given time intervals following the first search, and the stimulation energy level is adjusted accordingly.

According to another exemplifying embodiment, the detection of one or more losses of capture in one of the ventricles results in a decrease of the time period between successive searches for capture thresholds in the other ventricle. In other words, threshold searches are regularly performed at predefined or preprogrammed time intervals for the ventricle in which no capture detection is performed on beat-by-beat basis. When loss of capture has been detected in one ventricle, this triggers a change in the time interval between successive stimulation threshold searches. For instance, the threshold search interval could be decreased to half or a quarter of the regular search interval, or the threshold search could be reduced to a preselected time interval, such as one or a given number of hours. Preferably, the detected losses of capture trigger an immediate threshold search to be conducted.

The time interval between threshold searches is preferably restored to the predefined time interval following a selected number of searches or a selected time period. The selected time period could for instance be one such decreased time interval. However, repeated detection of capture loss during the period of shortened time interval will preferably result in the shortened interval being maintained. Then, each further trigger resulting from detected capture loss would preferably reset the count of said selected number of searches or selected time period before restoring the threshold search time interval.

According to yet another exemplifying embodiment, the action or preventive measure is an immediate increase in the safety margin for the other ventricle. Thus, upon detected of losses of capture in one of the ventricles, the setting for the stimulation energy content for stimulation pulses in the other ventricle is amended by increasing the safety margin. Thereby, the risk of capture losses occurring in the other ventricle, for instance due to a sudden increase in threshold level, is reduced. The increase of the safety margin is preferably between 0.1 to 1.0 Volt, more preferably between 0.2 and 0.6 Volt, and most preferred between 0.3 and 0.5 Volt.

According to one embodiment, the increased safety margin is maintained until the next regular threshold search has been performed. In another example, the increased safety margin could be applied during a selected time period and restored to its original setting if no losses of capture are determined during the selected time period.

According to a further exemplifying embodiment, an immediate threshold search is performed for the other ventricle as said preventive measure. Of course, if needed, the threshold search for the other ventricle is adapted to a possible threshold search for said one ventricle.

As understood by those skilled in the art, the different preventive measures or actions taken as described above can also be combined. As an example, and triggered by detected losses of capture in one ventricle, the safety margin could be increased and the time until the next threshold search be shortened in the other ventricle. Then, the increased safety margin would only be applied for a shorter period of time and energy would be preserved. In another example, the quick check for capture could, when negative, result in a decreased time interval between successive threshold searches and/or an increased safety margin being applied.

The trigger could be one single loss of capture in one ventricle for triggering said actions of the other ventricle. Preferably, though, a successive number of losses of capture is required in order to trigger said actions. In the most preferred case, two successive losses of capture triggers the preventive actions. However, other alternatives are also contemplated within the scope of the invention, such as any given number of successive losses or capture, or a given ratio of capture losses from a number of delivered pulses during a certain time period or a certain number of pulses. In one example, said trigger for the preventive actions in the other ventricle is predefined. According to another example, said trigger is a parameter selected by the physician.

Further objects and advantages of the present invention will be discussed below by means of exemplifying embodiments.

DESCRIPTION OF THE PREFERRED EMBODIMENTS

The following is a description of preferred embodiments in accordance with the present invention. This description is not to be taken in a limiting sense, but is made merely for the purpose of describing the general principles of the invention. Thus, even though a biventricular heart stimulator for sensing and stimulating in both the atria and ventricles will be described, the invention is also applicable to biventricular stimulators without atrial sensing and/or stimulation.

Figure 1:
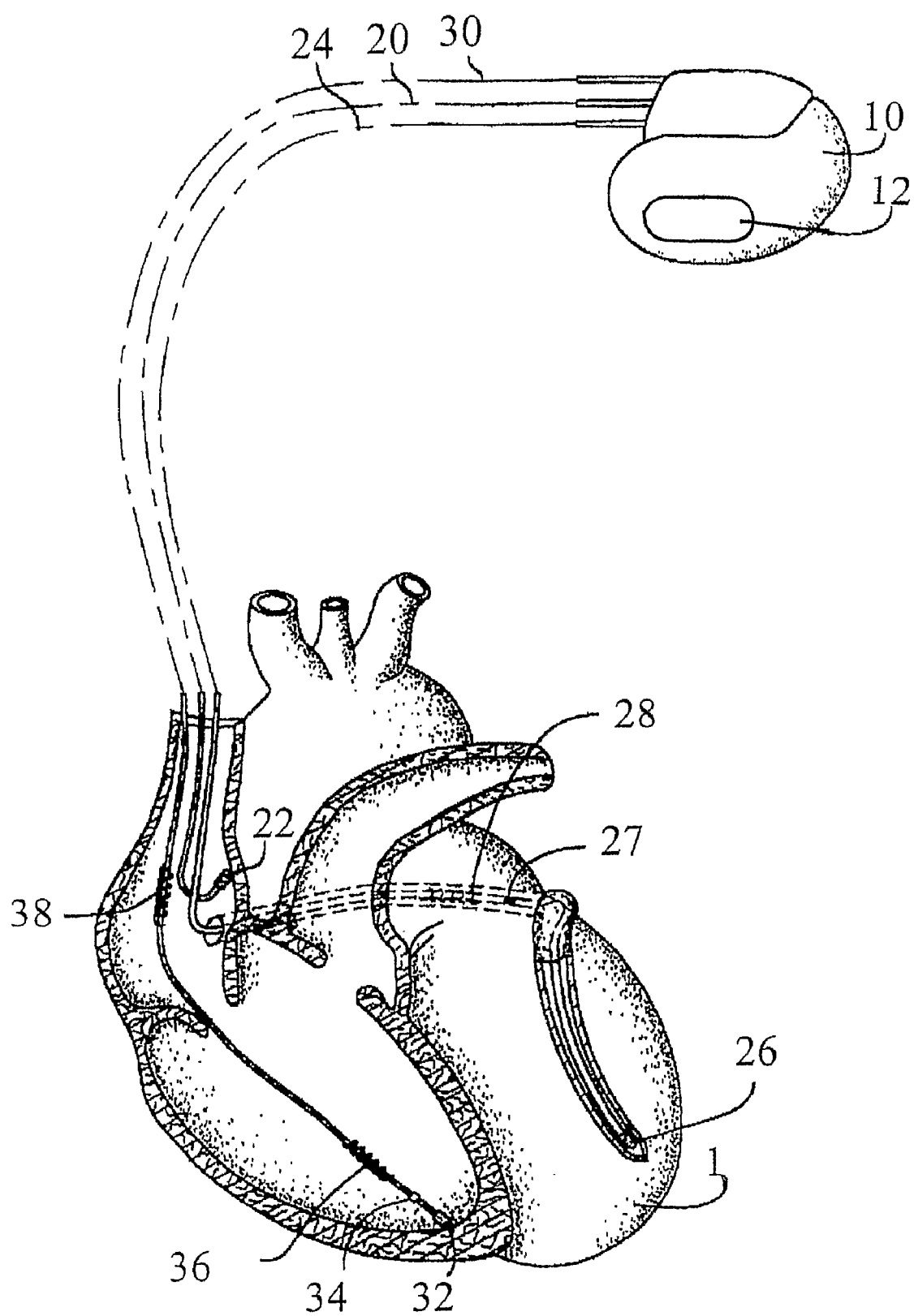
FIG. 1 is a simplified, partly cutaway view illustrating an implantable stimulation device in electrical communication via cardiac leads with a human heart for delivering multi-chamber stimulation and shock therapy.

With reference first to FIG. 1, there is shown a biventricular heart stimulator 10 in electrical communication with a human heart 1 via three cardiac leads 20, 24, and 30 suitable for delivering mufti-chamber stimulation and sensing. The stimulator could further be arranged to deliver cardioversion or shock therapy to the heart.

In order to sense atrial cardiac signals and to provide right atrial chamber stimulation therapy, the heart stimulator 10 is coupled to an implantable right atrial lead 20 having an atrial tip electrode 22, which typically is implanted in the right atrial appendage.

In order to sense left atrial and ventricular cardiac signals and to provide left-chamber pacing therapy, the heart stimulator 10 is coupled to a coronary sinus lead 24 designed for placement in the coronary sinus region, via the coronary sinus, so as to position a distal electrode adjacent to the left ventricle, and possible additional electrode(s) adjacent to the left atrium. As used herein, the phrase "coronary sinus region" refers to the vasculature of the left ventricle, including any portion of the coronary sinus, great cardiac vein, left marginal vein, left lateral vein, left posterior ventricular vein, middle cardiac vein, and/or small cardiac vein, or any other cardiac vein accessible via the coronary sinus.

Accordingly, the coronary sinus lead 24 is designed to receive atrial and ventricular cardiac signals and to deliver left ventricular pacing therapy using at least a left ventricular tip electrode 26, and left atrial pacing therapy using at least a left atrial ring electrode 27. In the illustrated example, an optional left atrial coil electrode 28 is also provided for delivering shocking therapy. A complete description of a coronary sinus lead can be found in U.S. Pat. No. 5,466,254, entitled "Coronary Sinus Lead with Atrial Sensing Capability" (Helland), which is incorporated herein by reference.

Furthermore, the heart stimulator 10 is in electrical communication with the heart 1 via a right ventricular lead 30 comprising, a right ventricular tip electrode 32, a right ventricular ring electrode 34, a right ventricular (RV) coil electrode 36, and a supraventricular (SV) coil electrode 38. Typically, the right ventricular lead 30 is transvenously inserted into the heart 1, for positioning the right ventricular tip electrode 32 in the right ventricular apex so that the RV coil electrode 36 is positioned in the right ventricle and the SVC coil electrode 38 is positioned in the superior vena cava. Accordingly, the right ventricular lead 30 is capable of receiving cardiac signals, and delivering stimulation in the form of pacing, cardioversion and shock therapy to the right ventricle.

Moreover, the heart stimulator 10 comprises electronic circuitry 12 and a battery (not shown). The electronic circuitry comprises at least one pulse generator for generating stimulation pulses to be delivered to the ventricles of the heart, and possibly to the atria thereof, sensing circuitry for receiving cardiac signals sensed by the cardiac leads 20, 24 and 30, and a controller. The controller controls both the sensing of cardiac signals and the delivery of stimulation pulses, for instance as to the duration, energy content and timing of the stimulation pulses.

In general biventricular operation, and in order to optimize the pacing therapy, a first stimulation pulse is normal first delivered to one ventricle of the heart. Then, following a short interventricular delay, generally in the range of 10 to 40 ms, a second stimulation pulse is delivered to the other ventricle. These will in the following be referred to as the first and the last ventricular pulses, as well as the first and the last ventricle. For most patients, in order to achieve the most effective pacing therapy in view of the present heart disorder, the first ventricle stimulated is the left ventricle, and the last ventricle stimulated is the right ventricle.

Furthermore, biventricular heart stimulators often, but not necessarily, have atrial stimulation functionality. Then, the heart stimulator delivers a respective atrial stimulation pulse before the delivery of the corresponding ventricular stimulation pulse. The time difference between these stimulation pulses is generally referred to as an AV-interval.

In the following, embodiments of the present invention will be described in more detail. It must be noted that, even though the following description is based on the assumption that capture detection on beat-by-beat basis is performed in the last ventricle, but not in the first, the description is also applicable to the reversed circumstances. In other words, "last ventricle" could be exchanged for "first ventricle" and vice versa in the following description and in the drawings. For ease of description, however, only the alternative of beat-by-beat capture detection in the last ventricle is described.

Figure 2:
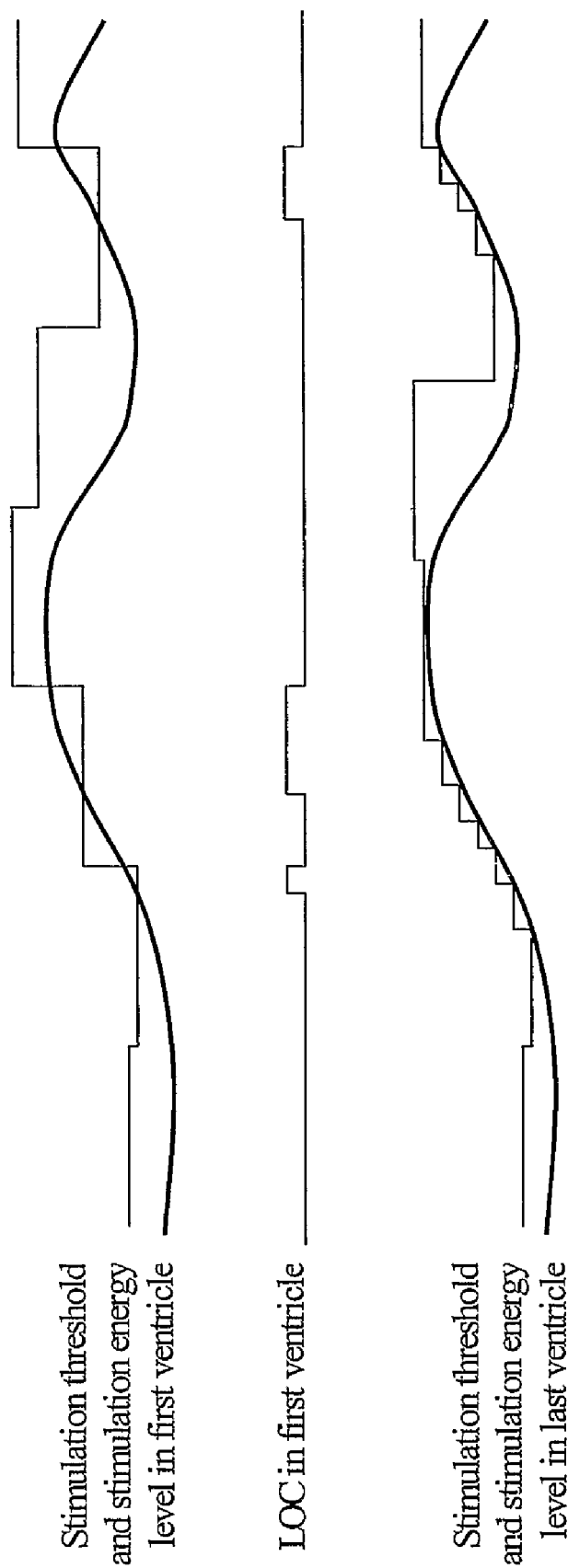
FIG. 2 is a schematic illustration of possible threshold levels, stimulation energy levels and loss of capture for a biventricular heart stimulator without the utilization of the present invention.

With reference now to FIG. 2, there is shown in schematical form, the variations in threshold levels for the first and the last ventricle over time, the corresponding adjustments and adaptations of the stimulation energy levels for both ventricles, and a timeline indicating the possible losses of capture (LOC) for the first ventricle. It should be noted that, for illustration purposes, the variations in capture thresholds have been exaggerated.

Turning first to the diagram for the last ventricle, it can be seen that the capture threshold, indicated by the bold line, varies over time. The thin line indicates the stimulation energy level, which is set to exceed the threshold level with a certain, preselected safety margin. Whenever a change in stimulation energy level can be seen in the figure, this has been preceded by a threshold search to update and store information regarding the capture or stimulation threshold for the ventricle. Even though losses of capture are not specifically indicated for the last ventricle, threshold searches performed during a period of increase of the capture threshold are generally triggered by a loss of capture. Thus, all but one of the threshold increments displayed in the stimulation energy level curve for the last ventricle corresponds to losses of capture.

Turning then to the diagram for the first ventricle, all variations of stimulation energy levels are preceded by a threshold search. These threshold searches are conducted at regular time intervals, which results in capture losses when the capture threshold in the time period between successive threshold searches has increased more than the applied safety margin. This is indicated in the diagram where the curve for capture threshold intersects the curve for the stimulation energy level. In the centre of the figure, there is indicated the time periods during which the capture threshold exceeds the energy content of the stimulation pulses. During these periods, there may be complete loss of capture in the first ventricle, with impaired pacing therapy as a result.

Figure 3:
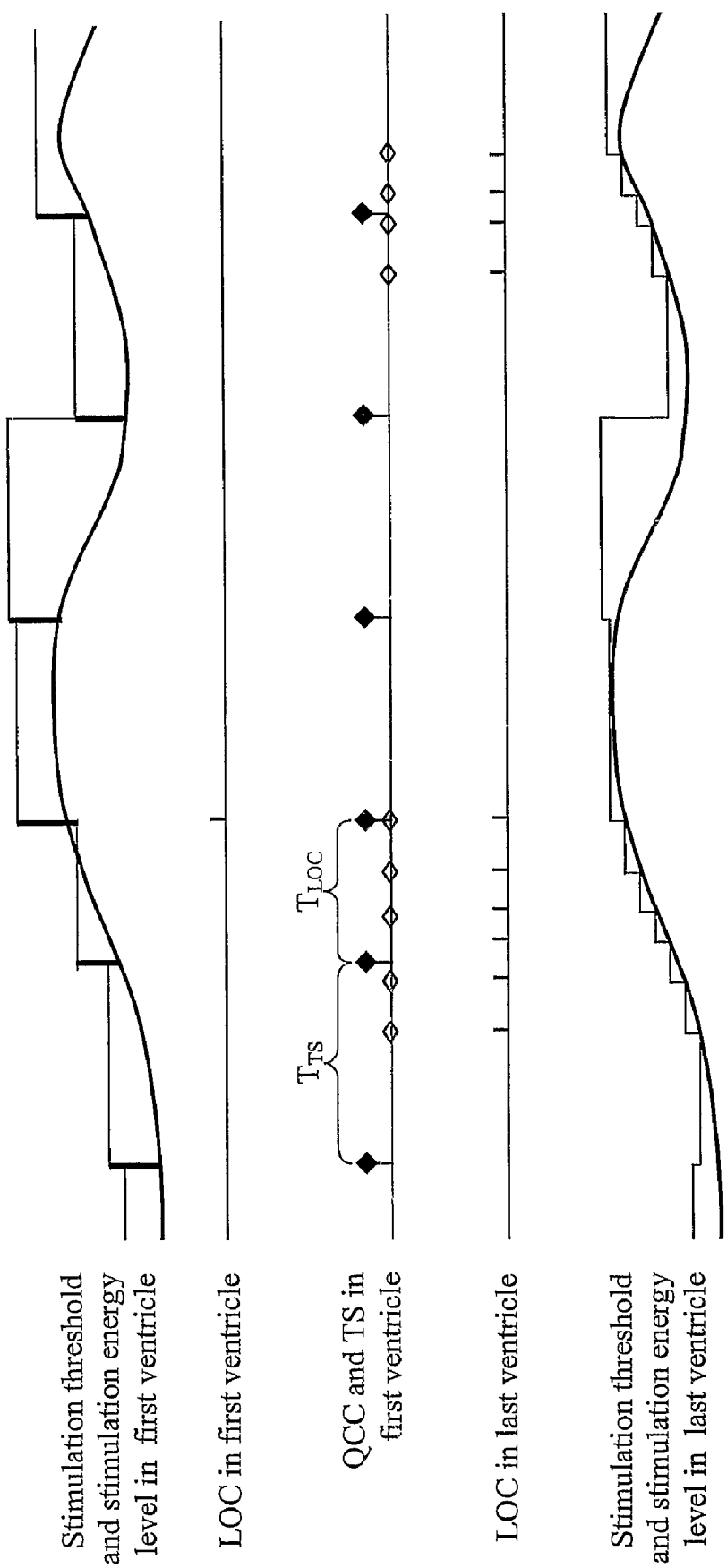
FIG. 3 is a schematic illustration of possible threshold levels, stimulation energy levels and loss of capture for a biventricular heart stimulator according to a first embodiment of the present invention.

With reference to FIG. 3, there will now be described a first preferred embodiment of the present invention. In the figure, there are five diagrams wherein the bottom diagrams show variation in stimulation thresholds and corresponding adjustments of stimulation energy levels for the ventricle in which capture is sensed on a beat-by-beat basis, and the occurrences of capture losses (LOC) in that ventricle. The bottom diagram is similar to the corresponding diagram shown in FIG. 2 and the description above relating to this ventricle also applies for the present embodiment, and also for the embodiments described below with reference to FIGS. 4 and 5. As stated above, this ventricle is referred to as the last ventricle. However, in particular circumstances, beat-by-beat basis could be performed in the first ventricle and disabled in the last. If so, the present embodiment and the embodiments to be described in the following would still be applicable.

The diagram at the centre shows the occurrences of threshold searches (TS) and immediate or quick checks for capture (QCC) in the other ventricle, which in this illustration is the first ventricle. Furthermore, the top diagrams show variations in stimulation thresholds and the adjustments of stimulation energy levels as a result of performed threshold searches, for the first ventricle, and the occurrences of capture losses (LOC) in the first ventricle.

As can be seen in FIG. 3, LOC in the last ventricle triggers a threshold search to be performed for that ventricle. In general, a first detected LOC triggers a change in the timing of the pacing pulses, e.g. a change in the atrioventricular or AV delay (interval between an atrial stimulation and the subsequent ventricular stimulation), the PV delay (interval between a sensed P wave and the subsequent ventricular stimulation), or the interventricular or VV delay. This is performed in order move the evoked response window, such that the result of the capture detection is not a misinterpretation of a fusion beat. If a second, subsequent LOC then occurs, this will trigger the above mentioned threshold search for the last ventricle.

Turning to the first ventricle, threshold searches are performed at regular time intervals $T_{TS}$, which is indicated in FIG. 3. Thus, the stimulation energy levels remain constant in the time interval between the threshold searches. Furthermore, in accordance with the most preferred embodiment of the invention, the LOC in the last ventricle also triggers the occurrence of a quick check for capture (QCC), which is indicated in the figure as un-filled rhombs. When performing a QCC for the first ventricle, the VV interval is changed such that the V pulse for the last ventricle is not delivered during the evoked response window used for the first ventricle. Then, a capture detection is performed for the first ventricle.

Of course, there are other methods for performing a quick check for capture in the first ventricle, one of which could include the omission altogether of one pacing pulse for the last ventricle in order to prevent the pulse from disturbing the evoked response detection for the first ventricle.

If the QCC confirms that there is capture in the first ventricle, nothing will happen. The stimulation energy level will remain constant until the next threshold search is performed. However, if the QCC reveals that there is LOC in the first ventricle, an immediate threshold search is conducted such that the stimulation energy levels can be adjusted in adaptation to the changed capture threshold. This results in the time interval between the last two threshold searches, referred to in the figure as $T_{LOC}$, being shorter than the regular threshold search interval. However, immediately following the threshold triggered by the LOC, the time interval is restored to $T_{TS}$, which generally is set at 8 hours. Alternatively, but not displayed in the figure, a shortened time interval, $T_{Temp}$, between the threshold search triggered by the LOC and the subsequent search could be used. For instance, this time interval could be $T_{Temp}=T_{TS}/2$, $T_{LOC}$, or any other suitable, e.g. preprogrammable time interval.

Figure 4:
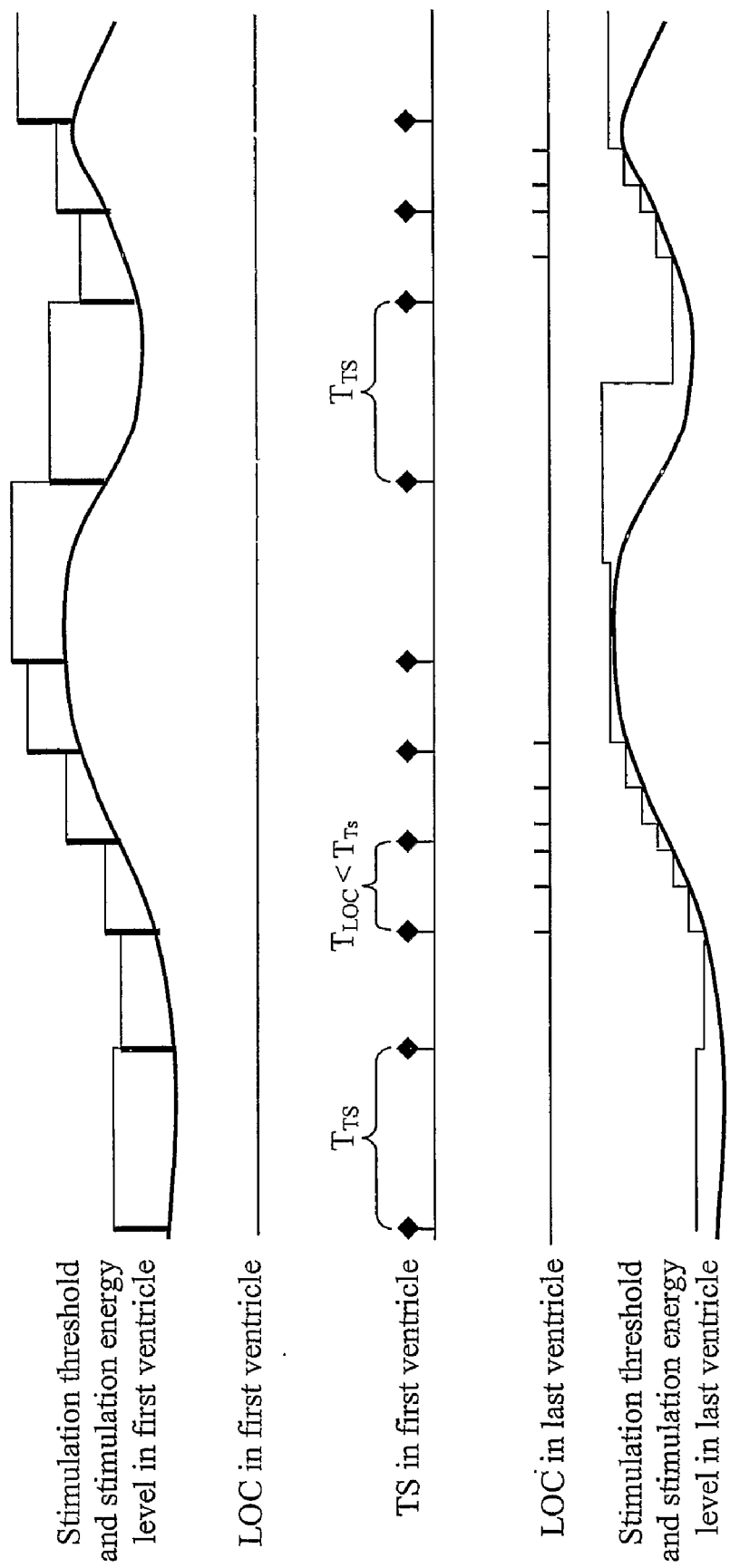
FIG. 4 is a schematic illustration of possible threshold levels, stimulation energy levels and loss of capture for a biventricular heart stimulator according to a second embodiment of the present invention.

Turning now to FIG. 4, a further exemplifying embodiment is illustrated. Beginning from the bottom of the figure, diagrams showing capture threshold variations, adjustments of stimulation energy levels, and occurrences of capture losses (LOC) in the last ventricle have been illustrated, in the manner as is described above in relation to FIG. 3.

The diagram at the centre of the figure shows the occurrences of threshold searches (TS) in the first ventricle. In the same manner in as in FIG. 3, the top diagram shows variations in stimulation thresholds and the adjustments of stimulation energy levels as a result of performed threshold searches in the first ventricle. Furthermore, there is also shown the occurrences of capture losses (LOC) in that ventricle, which in this illustration is none.

In this embodiment, the preventive action for the first ventricle triggered by detected LOC in the last ventricle is an adjustment of the time interval between successive threshold searches. Thus, the threshold search interval following detected LOC in the last ventricle, $T_{LOC}$, is less than the regular threshold search interval $T_{TS}$. Preferably, and as illustrated in the figure, $T_{LOC}=T_{TS}/2$. However, other suitable time intervals are also contemplated within the scope of the invention.

In the preferred example, the shortened time interval between successive threshold searches is maintained as long as there is repeated LOC in the last ventricle. In the illustrated embodiment, the threshold search interval is restored to the regular time interval $T_{TS}$ when no LOC has occurred during a shortened search interval $T_{LOC}$. In other words, at the expiry of a shortened time interval $T_{LOC}$ during which there has been no LOC in the last ventricle, the ongoing time interval is extended to the regular threshold search interval $T_{TS}$. As another example, one or more further shortened time intervals could be used before returning to the regular time interval $T_{TS}$. According to further examples, other selected time intervals during which the shortened threshold intervals are applied could be used.

Furthermore, in the illustrated embodiment, an immediate threshold search is carried out for the first ventricle in response to detected LOC in the last ventricle. Thereby, capture losses occurring in the first ventricle in the time period between the detected LOC in the last ventricle and subsequent threshold search in the first ventricle is eliminated. Moreover, the fact that a greater safety margin is used for the ventricle in which no beat-by-beat capture detection is performed, entails that for the vast majority of instances, ventricular losses of capture first occurs in the ventricle monitored on beat-by-beat basis. Thus, in the presently described embodiment, capture losses due to stimulation threshold changes may be virtually eliminated for the first ventricle.

According to a further embodiment, the detection of LOC in the last ventricle, preferably the detection of two successive LOC, triggers an immediate threshold search in the last ventricle, as well as an immediate threshold search in the first ventricle. In other words, whenever there is a threshold search in the last ventricle, there will also be a threshold search performed for the first ventricle.

Figure 5:
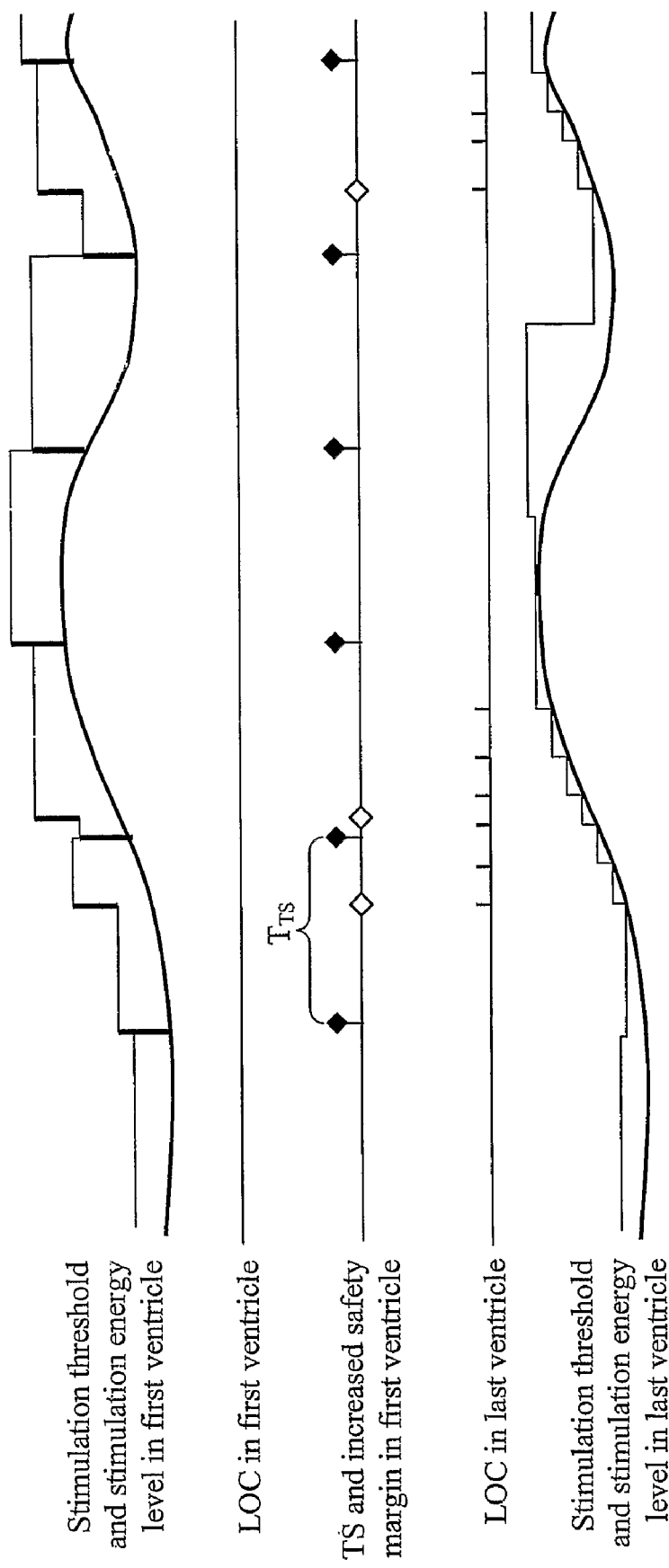
FIG. 5 is a schematic illustration of possible threshold levels, stimulation energy levels and loss of capture for a biventricular heart stimulator according to a third embodiment of the present invention.

With reference finally to FIG. 5, a further exemplifying embodiment will be described. In the figure, the bottom two diagrams are the same as those illustrated in FIGS. 3 and 4. The center diagram illustrates the instances at which threshold searches are performed, and at which an increased safety margin is applied, both illustrated events relating to the first ventricle. Similar to FIGS. 3 and 4, the top diagrams show variations in capture or stimulation thresholds, the adjustments of stimulation energy levels, and the occurrences of capture losses (LOC) in that ventricle, which in this illustration also is none.

As can be seen in the figure, threshold searches are conducted at regular time intervals for the first ventricle. The safety margin applied following each threshold search is the same, and is greater than the threshold margin used for the last ventricle. However, following detected LOC in the last ventricle, an increased safety margin is immediately applied to the stimulation energy level for the first ventricle in the manner as described above. Thereby, contrary to the situation described with reference to FIG. 2, an increase of the capture threshold for the first ventricle, during a time interval between successive threshold searches, which exceeds the regular safety margin, will thanks to the temporary increase in the safety margin not lead to loss of capture.

In the illustrated example, the safety margin is increased to twice the regular safety margin as a result of detected LOC in the last ventricle. Even though this is the preferred example, other examples are also contemplated within the scope of the invention. Furthermore, the increase in safety margin is preferably between 0.1 and 1.0 V, more preferably between 0.2 and 0.6 V, and even more preferably between 0.3 and 0.5 V. In the most preferred example, both the safety margin as well as the increase of the safety margin is 0.3 V. Preferably, the amount of safety margin increase, as well as the regular safety margin, is preprogrammed. However, either or both of the regular safety margin and the increase in safety margin could optionally be arranged to be programmable by the physician, in response to the needs and requirements for each particular patient.

In the present embodiment, the increased safety margin is maintained during a selected time period following the onset thereof. In the illustrated example, which is the most preferred alternative, the increased safety margin is maintained until the next ensuing threshold search in the first ventricle.

Even though the present invention has been described above using exemplifying embodiments thereof, alterations, modifications and combinations thereof may be made within the scope of the invention, as defined in the accompanying claims. For instance, the quick check for capture triggered by LOC in the last ventricle, as described with reference to FIG. 3, could be combined with an increase in safety margin following a detected LOC in the first ventricle. Then, the increased safety margin could be maintained until the next threshold search, and there would be no need for an immediate threshold search as a result of the detected LOC in the first ventricle.

Although modifications and changes may be suggested by those skilled in the art, it is the intention of the inventors to embody within the patent warranted heron all changes and modifications as reasonably and properly come within the scope of their contribution to the art.

We claim as our invention:

1. A biventricular heart stimulator for stimulating both ventricles of a human heart, comprising
    a pulse generator for delivering stimulation pulses of varying amplitudes,
    electrode leads for transmitting stimulation pulses from the pulse generator to a first and to a second of said ventricles, and for transmitting electric signals from the ventricles of the heart to the heart stimulator;
    a control unit for controlling the pulse generator, said control unit being configured to control the delivery of said pulses such that stimulation pulses in a single heart beat cycle are respectively first delivered to the first of said ventricles and then to the second of said ventricles;
    a sensing circuit configured to check for capture or loss of capture in one of said ventricles in response to delivered stimulation pulses, said sensing circuit being controlled by said control unit and arranged to receive said electric signals transmitted by said electronic leads;
    the control unit being configured to perform, as a result of loss of capture determined in said one ventricle by said sensing circuit, a preventive measure for prevention of loss of capture in the other ventricle, as a result of at least two successive losses of capture;
    said sensing circuit being also configured to check for capture or loss of capture in the other ventricle, and said control unit being configured to effect an immediate check for capture in the other ventricle as said preventive measure; and
    said control unit being further configured to perform threshold searches for determining a threshold value for the amplitude of a stimulation pulse that is required for effectuating capture, and for setting the pulse amplitude of the stimulation pulses to a value exceeding said determined threshold value by a selected margin, and to perform such a threshold search in said other ventricle as a result of determined loss of capture in said other ventricle, as a result of said at least two successive losses of capture.

2. The heart stimulator as claimed in claim 1, wherein said control unit is configured to perform a further threshold search in said other ventricle after a selected time period as a result of said determined loss of capture in said other ventricle.

3. The heart stimulator as claimed in claim 1, wherein the control unit is configured to perform an immediate threshold search in said other ventricle as a result of said determined loss of capture in said one ventricle.

4. The heart stimulator as claimed in claim 1, wherein said one ventricle is said first ventricle and said other ventricle is said second ventricle.

5. The heart stimulator as claimed in claim 1, wherein said one ventricle is said second ventricle and said other ventricle is said first ventricle.

6. A biventricular heart stimulator for stimulating both ventricles of a human heart, comprising:
    a pulse generator for delivering stimulation pulses of varying amplitudes,
    electrode leads for transmitting stimulation pulses from the pulse generator to a first and to a second of said ventricles, and for transmitting electric signals from the ventricles of the heart to the heart stimulator;
    a control unit for controlling the pulse generator, said control unit being configured to control the delivery of said pulses such that stimulation pulses in a single heart beat cycle are respectively first delivered to the first of said ventricles and then to the second of said ventricles;
    a sensing circuit configured to check for capture or loss of capture in one of said ventricles in response to delivered stimulation pulses, said sensing circuit being controlled by said control unit and arranged to receive said electric signals transmitted by said electronic leads;

the control unit being configured to perform, as a result of loss of capture determined in said one ventricle by said sensing circuit, a preventive measure for prevention of loss of capture in the other ventricle, as a result of at least two successive losses of capture; and said control unit is being further configured to perform threshold searches for determining a threshold value for the stimulation pulse amplitude required for effectuating capture, and to set the pulse amplitude of the stimulation pulses to a value exceeding said determined threshold value by a selected margin, and to perform said threshold searches at preselected time intervals, and to temporarily decrease said preselected time interval between successive threshold searches in said other ventricle as a result of said determined loss of capture in said one ventricle.

7. The heart stimulator as claimed in claim 6, wherein the control unit is configured to decrease said preselected time interval by half as the result of said determined loss of capture in said one ventricle.

8. The heart stimulator as claimed in claim 6, wherein the control unit is configured to restore the time interval between successive threshold searches to said preselected time interval if no losses of capture are determined in said one ventricle within a selected time period.

9. The heart stimulator as claimed in claim 8, wherein said selected time period corresponds to said decreased time interval.

10. The heart stimulator as claimed in claim 9, wherein the control unit is further configured to perform threshold searches for determining a threshold value for the stimulation pulse amplitude required for effectuating capture, and setting the pulse amplitude of the stimulation pulses to a value exceeding said determined threshold value by a selected margin, and wherein the control unit is configured to temporarily increase said selected margin as a result of said determined loss of capture in said one ventricle.

11. The heart stimulator as claimed in claim 10, wherein the control unit is configured to increase said selected margin by between 0.1 and 1.0 V, preferably between 0.2 and 0.6 V, and more preferably between 0.3 and 0.5 V.

12. The heart stimulator as claimed in claim 10, wherein the control unit is configured to maintain said increased selected margin until a threshold search is performed.

13. The heart stimulator as claimed in claim 10, wherein the control unit is configured to restore said selected margin if no losses of capture are determined in said one ventricle within a selected time period.

14. The heart stimulator as claimed in claim 8, wherein said control unit is configured to perform said threshold searches at preselected time intervals, wherein said selected time period corresponds to said preselected time interval.

15. A method of controlling a biventricular heart stimulator for stimulating both ventricles of a human heart, comprising the steps of:
delivering successive stimulation pulses to a first and a second ventricle of the heart such that stimulation pulses in a single heart beat cycle is first delivered to the first ventricle and then to the second ventricle;
determining capture or loss of capture by the heart in response to stimulation pulses delivered to one of said ventricles;
performing as a result of detected loss of capture in said one ventricle, preventive measures for prevention of loss of capture in the other ventricle, preferably as a result of at least two successive losses of capture in said one ventricle,
checking for capture or loss of capture in the other ventricle;
performing an immediate check for capture in the other ventricle as said preventive measures;
performing threshold searches for determining a threshold value for the amplitude of a stimulation pulse that is required for effectuating capture,
setting the pulse amplitude of the stimulation pulses to a value exceeding said determined threshold value by a selected margin, and
performing such a threshold search in said other ventricle as a result of determined loss of capture in said other ventricle, preferably as a result of at least two successive losses of capture.

16. The method as claimed in claim 15, further comprising the step of:
performing a further threshold search in said other ventricle after a selected time period as a result of said determined loss of capture in said other ventricle.

17. The method as claimed in claim 15, further comprising the step of:
performing an immediate threshold search in said other ventricle as a result of said determined loss of capture in said one ventricle.

18. The method as claimed in claim 15, wherein said one ventricle is said first ventricle and said other ventricle is said second ventricle.

19. The method as claimed in claim 15, wherein said one ventricle is said second ventricle and said other ventricle is said first ventricle.

20. A method of controlling a biventricular heart stimulator for stimulating both ventricles of a human heart comprising the steps of:
delivering successive stimulation pulses to a first and a second ventricle of the heart such that stimulation pulses in a single heart beat cycle is first delivered to the first ventricle and then to the second ventricle;
determining capture or loss of capture by the heart in response to stimulation pulses delivered to one of said ventricles;
performing as a result of detected loss of capture in said one ventricle, preventive measures for prevention of loss of capture in the other ventricle, preferably as a result of at least two successive losses of capture in said one ventricle;
performing threshold searches for determining a threshold value for the stimulation pulse amplitude required for effectuating capture,
setting the pulse amplitude of the stimulation pulses to a value exceeding said determined threshold value by a selected margin,
performing said threshold searches at preselected time intervals, and
temporarily decreasing said preselected time interval between successive threshold searches in said other ventricle as a result of said determined loss of capture in said one ventricle.

21. The method as claimed in claim 20, further comprising the step of:
decreasing said preselected time interval by half as the result of said determined loss of capture in said one ventricle.

22. The method as claimed in claim 20, further comprising the step of:

restoring the time interval between successive threshold searches to said preselected time interval if no losses of capture are determined in said one ventricle within a selected time period.

23. The method as claimed in claim 22, wherein said selected time period corresponds to said decreased time interval.

24. The method as claimed in claim 22, comprising performing said threshold searches at preselected time intervals, and wherein said selected time period corresponds to said preselected time interval.

25. A method of controlling a biventricular heart stimulator for stimulating both ventricles of a human heart comprising the steps of:
- delivering successive stimulation pulses to a first and a second ventricle of the heart such that stimulation pulses in a single heart beat cycle is first delivered to the first ventricle and then to the second ventricle;
- determining capture or loss of capture by the heart in response to stimulation pulses delivered to one of said ventricles;
- performing as a result of detected loss of capture in said one ventricle, preventive measures for prevention of loss of capture in the other ventricle, preferably as a result of at least two successive losses of capture in said one ventricle;
- performing threshold searches for determining a threshold value for the stimulation pulse amplitude required for effectuating capture,
- setting the pulse amplitude of the stimulation pulses to a value exceeding said determined threshold value by a selected margin, and
- temporarily increasing said selected margin as a result of said determined loss of capture in said one ventricle.

26. The method as claimed in claim 25, further comprising the step of:
- increasing said selected margin by between 0.1 and 1.0 V, preferably between 0.2 and 0.6 V, and more preferably between 0.3 and 0.5 V.

27. The method as claimed in claim 25, further comprising the step of:
- maintaining said increased selected margin until a threshold search is performed.

28. The method as claimed in claim 25, further comprising the step of:
- restoring said selected margin if no losses of capture are determined in said one ventricle within a selected time period.

* * * * *